US012703861B2

(12) United States Patent
Zhang et al.

(10) Patent No.: US 12,703,861 B2
(45) Date of Patent: Aug. 11, 2026

(54) SGRNA GUIDING PD1 GENE FOR CLEAVAGE TO ACHIEVE EFFICIENT INTEGRATION OF EXOGENOUS SEQUENCES

(71) Applicant: BRL Medicine (Shanghai) Co., Ltd., Shanghai (CN)

(72) Inventors: Jiqin Zhang, Shanghai (CN); Jiaxuan Yang, Shanghai (CN); Yue Tian, Shanghai (CN); Bing Du, Shanghai (CN); Dali Li, Shanghai (CN); Mingyao Liu, Shanghai (CN); Zaixi Xi, Shanghai (CN)

(73) Assignee: BRL Medicine (Shanghai) Co., Ltd., Shanghai (CN)

( * ) Notice: Subject to any disclaimer, the term of this patent is extended or adjusted under 35 U.S.C. 154(b) by 1134 days.

(21) Appl. No.: 17/628,231

(22) PCT Filed: Jul. 9, 2020

(86) PCT No.: PCT/CN2020/101073

§ 371 (c)(1),
(2) Date: Jan. 19, 2022

(87) PCT Pub. No.: WO2021/012960

PCT Pub. Date: Jan. 28, 2021

(65) Prior Publication Data

US 2022/0356456 A1 Nov. 10, 2022

(30) Foreign Application Priority Data

Jul. 19, 2019 (CN) ......................... 201910653711.1

(51) Int. Cl.

| | |
|---|---|
| ***C12N 9/22*** | (2006.01) |
| ***A61K 40/11*** | (2025.01) |
| ***A61K 40/31*** | (2025.01) |
| ***A61K 40/42*** | (2025.01) |
| ***C07K 14/705*** | (2006.01) |
| ***C07K 14/725*** | (2006.01) |
| ***C12N 5/0783*** | (2010.01) |
| ***C12N 15/11*** | (2006.01) |
| ***C12N 15/62*** | (2006.01) |
| ***C12N 15/90*** | (2006.01) |

(52) U.S. Cl.

CPC ................ *C12N 9/22* (2013.01); *A61K 40/11* (2025.01); *A61K 40/31* (2025.01); *A61K 40/4211* (2025.01); *A61K 40/4224* (2025.01); *C07K 14/7051* (2013.01); *C12N 5/0636* (2013.01); *C12N 15/11* (2013.01); *C12N 15/625* (2013.01); *C12N 15/907* (2013.01); *A61K 2239/48* (2023.05); *C12N 2310/20* (2017.05); *C12N 2800/80* (2013.01)

(58) Field of Classification Search

None

See application file for complete search history.

(56) References Cited

U.S. PATENT DOCUMENTS

| | | | |
|---|---|---|---|
| 2017/0152506 | A1 | 6/2017 | Wagner et al. |
| 2018/0325955 | A1 | 11/2018 | Terrett et al. |

FOREIGN PATENT DOCUMENTS

| | | | |
|---|---|---|---|
| CN | 103820454 | A | 5/2014 |
| CN | 106399375 | A | 2/2017 |
| CN | 108531457 | A | 9/2018 |
| CN | 108753817 | A | 11/2018 |
| CN | 108949693 | A | 12/2018 |
| CN | 109517796 | A | 3/2019 |
| CN | 109652380 | A | 4/2019 |
| CN | 109652381 | A | 4/2019 |
| WO | 2018233596 | A1 | 12/2018 |

OTHER PUBLICATIONS

Muller et al. "*Streptococcus thermophilus* CRISPR-Cas9 Systems Enable Specific Editing of the Human Genome" (Mar. 2016), Gene & Cell Therapy, vol. 24, No. 3, 636-644. (Year: 2016).*

Zhaoqin Fang, CRISPR-Cas9 Gene Editing, The Application of Molecular Biology Technology in TCM Studies, Apr. 30, 2018, p. 195-204, Shanghai Scientific & Technical Publishers.

J. Sambrook, et al., Molecular Cloning A Laboratory Manual, 1989, Second Edition, Cold Spring Harbor Laboratory Press.

Xiaoyun Dai, et al., One-step generation of modular CAR-T cells with AAV-Cpf1, Nature Methods, 2019.

Wanghong Hu, et al., CRISPR/Cas9-mediated PD-1 disruption enhances human mesothelin-targeted CAR T cell effector functions, Cancer Immunology, Immunotherapy, 2019, pp. 365-377, vol. 68, Springer.

Evi J. Rupp, et al., CRISPR/Cas9-mediated PD-1 disruption enhances anti-tumor efficacy of human chimeric antigen receptor T cells, Scientific Reports, 2017, pp. 1-10, 7:737.

Zhilong Zhao, et al., CRISPR knock out of programmed cell death protein 1 enhances anti-tumor activity of cytotoxic T lymphocytes, Oncotarget, 2018, pp. 5208-5215, vol. 9, No. 4.

Shu Su, et al., CRISPR-Cas9 mediated efficient PD-1 disruption on human primary T cells from cancer patients, Scientific Reports, 2016, pp. 1-13, 6:20070.

* cited by examiner

*Primary Examiner* — Teresa E Knight

(57) ABSTRACT

Disclosed is an sgRNA guiding a PD1 gene for cleavage to achieve the efficient integration of exogenous sequences. The method for gene editing a PD1 gene in cells includes the steps of introducing a nuclease and an sgRNA into cells, and gene-editing the PD1 gene. The sgRNA guides the nuclease to cleave the PD1 gene and forms a broken site, at which an exogenous donor repair template can also be introduced, so that CAR-T elements can be directionally inserted at the specific site of the PD1 locus to construct enhanced CD19-CART cells with PD1 knockout in one step.

9 Claims, 7 Drawing Sheets

Specification includes a Sequence Listing.

SGRNA GUIDING PD1 GENE FOR CLEAVAGE TO ACHIEVE EFFICIENT INTEGRATION OF EXOGENOUS SEQUENCES

CROSS REFERENCE TO THE RELATED APPLICATIONS

This application is the national phase entry of International Application No. PCT/CN2020/101073, filed on Jul. 9, 2020, which is based upon and claims priority to Chinese Patent Application No. 201910653711.1, filed on Jul. 19, 2019, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named GBBJQH006_Sequence Listing.txt, created on 01/17/2022, and is 3,988 bytes in size.

TECHNICAL FIELD

The present disclosure relates to a nucleotide, in particular to an sgRNA, and the sgRNA is able to guide to cleave the PD1 locus to achieve the efficient integration of exogenous sequences at this site.

BACKGROUND

Chimeric antigen receptor T-cell (CAR-T) technology is a novel adoptive immunotherapy emerged in recent years. In the technology, T cells of a patient are genetically modified in vitro, and are transfused back into the body of the patient after certain expansion, thereby realizing targeting killing of tumors. A CAR-T structure mainly includes a single chain antibody which extracellularly and specifically recognizes tumor specific antigens, a transmembrane domain, and a serial signal domain for intracellularly activating T cells (CD28-CD3z and 4-1BB-CD3z are widely used at present). Since Science selected the tumor immunotherapy technology as the top 10 technological breakthroughs of the year in 2013, research in this field has developed vigorously. At present, two CAR-T products have been proved by the U.S. Food and Drug Administration for the clinic treatment of hematological malignancies, which marks a great success of the CAR-T technology. However, as an emerging technology, the CAR-T technology still faces a lot of challenges in every respect, thus there is a huge room for improvement.

CRISPR/Cas9 system is an acquired immune mechanism derived from archaea and bacteria and used for resisting the invasion of an exogenous DNA fragment such as plasmid and bacteriophage. This system mainly functions by a CRISPR sequence and a locus encoding Cas protein, the most commonly used at present is Cas9 nuclease of type II family, and such a system can play a role only by a single effector protein. When an exogenous DNA invades bacteria, type II CRISPR system firstly integrates the invading DNA between CRISPR repetitive sequences. Subsequently, a CRISPR RNA (crRNA) including the invading DNA sequence is transcribed and processed. After this, a transactivating CRISPR RNA (tracrRNA) binds to the crRNA, and finally forms a complex with a Cas9 protein. Finally, the Cas9 protein acts as an endonuclease through its HNH and RuvC-like domain to trigger double-strand breakage of DNA. The double-strand breakage of the DNA may trigger a damage repair mechanism, thereby realizing editing of a specific gene by methods such as homologous recombination. So far, the CRISPR/Cas9 technology has been successfully applied in many fields, showing a broad prospect.

PD-1 is an important immunosuppressive transmembrane protein expressed on the surface of T cells, and has two ligands, i.e., PD-L1 and PD-L2. Studies found that tumor cells can highly express a PD-L1 to activate a PDL1/PD1 pathway, resulting in phosphorylation of an intracellular domain of PD-1 and recruitment of tyrosine phosphatase SHP-2, thereby reducing activation of a TCR signal pathway and inhibiting activation of T cells. Clinical studies have shown that blocking the PDL1/PD1 pathway can remove inhibition on T cells and play a tumor-killing role. At present, a variety of antibody drugs which block the PDL1/PD1 pathway have been approved by the U.S. Food and Drug Administration for the treatment of various malignant tumors such as non-small cell lung cancer and melanoma, which show good efficacy, and marks a great success of PD1 immune checkpoint therapy.

In order to enhance the anti-tumor effect of the CAR-T cells, the present disclosure cleaves a DNA at a specific site of PD1 locus by using the gene editing technology, and meanwhile introduces an exogenous target gene, thus enlarging the application space of the CAR-T technology.

SUMMARY

The present disclosure provides a method for gene editing a PD1 gene.

In the present disclosure, "gene editing" refers to substitution, deletion and/or insertion at a target of the gene of the cell. In one embodiment, gene editing can produce a DNA mutation at the target of the cell by introducing one or more natural or artificially engineered nucleases into cells; in other embodiments, an exogenous donor repair template can be provided.

In the present disclosure, a nuclease can be introduced into cells by using a conventional technology in the art, for example, the nuclease can be introduced into cells by using vector transformation, microinjection, transfection, lipid transfection, heat shock, electroporation, transduction, gene gun, microinjection, DEAE-glucan mediated transfer, etc.; in preferred embodiments, the cells may be T cells; the introduction method may adopt electroporation.

"T cells" or "T lymphocytes" are recognized in the art to include thymocytes, native T lymphocyts, immature T lymphocytes, mature T lymphocytes, resting T lymphocytes or activated T lymphocytes. T cells may be T helper (Th) cells, for example, T helper 1 (Th1) cells or T helper 2 (Th2) cells. T cells may be helper T cells (HTL; CD4+T cells), CD4+T cells, cytotoxic T cells (CTL; CD8+T cells), tumor infiltrating cytotoxic T cells (TIL; CD8+T cells), CD4+CD8+T cells, CD4-CD8−T cells or any other T cell subpopulations. In one embodiment, T cells may be NKT cells. In a preferred embodiment, T cells are modified to express a CAR.

In the present disclosure, the PD1 gene in cells can be edited by using a nuclease, and the nuclease can bind to and cleave a target sequence on the PD1 gene. The nuclease can be used to introduce a double-strand breakage into a target polynucleotide sequence, and the double-strand breakage can be repaired by a non-homologous end joining (NHEJ) in the absence of a polynucleotide template (e.g., a donor repair template), or can be repaired by homologous directed repair (HDR) i.e., homologous recombination in the presence of the donor repair template.

In the present disclosure, nuclease refers to a nuclease including one or more DNA binding domains and one or more DNA cleavage domains. The nuclease in the present disclosure can be designed and/or modified from a naturally occurring nuclease or from an artificially engineered nuclease. The nuclease of the present disclosure includes a homing endonuclease, megaTALs, a transcription activator like effector nuclease (TALEN), a zinc finger nuclease (ZFN) and a clustered regularly interspaced short palindromic repeats CRISPR/Cas nuclease system. In a preferred embodiment, the nuclease of the present disclosure includes a CRISPR/Cas nuclease system.

In the present disclosure, the CRISPR/Cas nuclease system includes a Cas nuclease and one or more RNAs which recruit the Cas nuclease to the target, e.g., a transactivating crRNA (tracrRNA) and a CRISPR RNA (crRNA) or a single guide RNA (sgRNA). The crRNA and the tracrRNA can design one polynucleotide sequence of the "single guide RNA" or "sgRNA".

In one embodiment, the Cas nuclease includes double-stranded DNA endonuclease activity or nickase activity, and forms a target complex with the crRNA and the tracrRNA or the sgRNA for site-specific DNA recognition and site-specific cleavage of a protospacer target sequence located within the PD1 locus. A protospacer motif adjoins a short protospacer adjacent motif (PAM), and plays a role in recruitment of the Cas/RNA complex. Cas polypeptide recognizes a PAM motif that is specific to the Cas polypeptide.

In the present disclosure, Cas enzyme is type I or type III Cas enzyme, preferably the type II Cas enzyme. The type II Cas enzyme in the present disclosure may be any Cas enzyme, including but not limited to Cas9, Cas3, Cas8a, Cas8b, Cas10d, Cse1, Csy1, Csn2, Cas4, Cas10, Csm2, Cmr5, Fok1 as well as other nucleases known in the art and any combination thereof.

In a preferred embodiment, the Cas enzyme of the present disclosure is Cas9, more preferably, the Cas9 enzyme is originated from *Streptococcus pneumoniae, Streptococcus pyogenes* or *Streptococcus thermophilus*, "being originated from *Streptococcus pneumoniae, Streptococcus pyogenes* or *Streptococcus thermophilus*" here should be understood as coming from or being derived from *Streptococcus pneumoniae, Streptococcus pyogenes* or *Streptococcus thermophilus*. A derived enzyme means that it has a high degree of sequence homology to a wild-type enzyme, for example, it has been mutated or modified at certain sites.

In some embodiments, the Cas enzyme includes one or more mutations selected from the following group: D10A, E762A, H840A, N854A, N863A or D986A and/or one or more other mutations in RuvC1 or HNH domain of the Cas enzyme. In a preferred embodiment, the Cas enzyme mutation includes: *Streptococcus pyogenes* (D10A), *Streptococcus thermophilus* (D9A), *Treponema denticola* (D13 A), *Neisseria meningitidis* (D16A), *Streptococcus pyogenes* (D839A, H840A or N863A), *Streptococcus thermophilus* (D598A, H599A or N622A), *Treponema denticola* (D878A, H879A or N902A), and *Neisseria meningitidis* (D587A, H588A or N611A).

In one embodiment, the Cas enzyme has one or more mutations in a catalytic domain, wherein during the transcription, a tracr matched sequence hybridizes to a tracr sequence, and a guide sequence guides sequence-specific binding of the CRISPR complex to the target sequence, and wherein the enzyme further includes one functional domain.

In other embodiments, a suitable Cas9 polypeptide can also be obtained from the following species: *Enterococcus faecium, Enterococcus, Listeria innocua, Listeria monocytogenes, Listeria seeligeri, Listeria ivanovii, Streptococcus agalactiae, Streptococcus anginosus, Streptococcus bovis, Streptococcus dysgalactiae, Streptococcus equinus, Streptococcus gallolyticus, Streptococcus macacae, Streptococcus mutans, Streptococcus pseudoporcinus, Streptococcus pyogenes, Streptococcus thermophilus, Streptococcus gordonii, Streptococcus infantarius, Streptococcus equi, Streptococcus mitis, Streptococcus pasteurianus, Streptococcus suis, Streptococcus vestibularis, Streptococcus sanguis, Streptococcus downei*, rod-shaped *Neisseria, Neisseria cinerea, Neisseria flavescens, Neisseria lactamica, Neisseria meningitidis, Neisseria flavescens, Lactobacillus brevis, Lactobacillus buchneri, Lactobacillus casei*, lactic acid bacteria, *Lactobacillus fermentium, Lactobacillus gasseri, Lactobacillus jensenii, Lactobacillus johnsonii, Lactobacillus rhamnosus, Lactobacillus ruminis, Lactobacillus salivarius, Lactobacillus sanfranciscensis, Corynebacterium accolens, Corynebacterium diphtheriae, Corynebacterium matruchotii, Campylobacter jejuni, Clostridium perfringens, Treponema vincentii, Treponema phageaenae* and *Treponema denticola.*

In other embodiments, the nuclease may also be selected from Cpf1, and the Cpf1 can be obtained from the bacterial species including but not limited to: *Francisella, Acidaminococcus, Brucella* and *Lachnospira.*

In the present disclosure, the guide nucleotide sequence sgRNA is specific to a gene and targets the gene to conduct Cas endonuclease-induced double-strand breakage. The sequence in the guide nucleotide sequence may be in a locus of the gene. In one embodiment, the length of the guide nucleotide sequence is at least 10, 11, 12, 13, 14, 15, 16, 17, 18, 19, 20, 21, 22, 23, 24, 25, 26, 27, 30, 31, 32, 33, 34, 35, 36, 37, 38, 39, 40 or more nucleotides.

The guide nucleotide sequence may be specific to any gene, and in the present disclosure, the sgRNA is specific to the PD1 gene.

In the present disclosure, a donor repair template includes one or more homologous arms. The "homologous arm" refers to a nucleotide sequence, that is exactly the same or almost exactly the same as the DNA sequence on two sides of the DNA breakage introduced at the target by the nuclease, in the donor template.

In one embodiment, the donor template includes a 5' homologous arm, and the 5' homologous arm includes a nucleotide sequence that is exactly the same or almost exactly the same as the DNA sequence at 5' of a DNA broken site. In other embodiments, the donor template includes a 3' homologous arm, and the 3' homologous arm includes a nucleotide sequence that is exactly the same or almost exactly the same as a DNA sequence at 3' of the DNA broken site. In a preferred embodiment, the donor template includes a 5' homologous arm and a 3' homologous arm.

The homologous arm of the present disclosure has a suitable length, including but not limited to 100 bp to 3000 bp, in specific embodiments, the length of the homologous arm may be selected from 100 bp, 200 bp, 300 bp, 400 bp, 500 bp, 600 bp, 700 bp, 800 bp, 900 bp, 1000 bp, 1100 bp, 1200 bp, 1300 bp, 1400 bp, 1500 bp, 1600 bp, 1700 bp, 1800 bp, 1900 bp, 2000 bp, 2100 bp, 2200 bp, 2300 bp, 2400 bp, 2500 bp, 2600 bp, 2700 bp, 2800 bp, 2900 bp or 3000 bp or longer homologous arm, and homologous arms including all intermediate lengths.

In a preferred embodiment, the donor template includes a 5' homologous arm, a CAR and a 3' homologous arm.

In a preferred embodiment, the CAR is inserted into the locus of PD1 by an exogenous donor template including the chimeric antigen receptor (CAR).

The CAR is a molecule that combines antibody-based specificity against a target antigen (e.g. a tumor antigen) with a T cell receptor activated intracellular domain to produce a chimeric protein, and the chimeric protein shows a specific anti-tumor cellular immunity activity.

In the present disclosure, the CAR includes an extracellular domain that binds to a specific target antigen (also referred to as a binding domain or antigen specific binding domain), a transmembrane domain and an intracellular signaling domain.

In one embodiment, the CAR includes an extracellular binding domain that specifically binds to a target polypeptide (e.g., target antigen) expressed on tumor cells. The binding domain may include any protein, polypeptide, oligopeptide or peptide having an ability to specifically recognize and bind to a biomolecule (e.g., cell surface receptor or tumor protein, lipid, polysaccharide or other cell surface target molecules or components thereof). The binding domain includes any naturally occurring, synthetic, semi-synthetic or recombinant binding partner of a biomolecule of interest.

Further, the extracellular binding domain includes an antibody or an antigen-binding fragment thereof.

The antibody refers to a binding agent as a polypeptide including at least a light chain or heavy chain immunoglobulin variable region that specifically recognizes and binds to an epitope of a target antigen, such as peptide, lipid, polysaccharide or a nucleotide containing a antigenic determinant, such as a nucleotide recognized by immune cells. The antibody includes an antigen-binding fragment, for example, camel Ig (Camelidae antibody or its VHH fragment), Ig NAR, Fab fragment, Fab' fragment, F(ab)'2 fragment, F(ab)'3 fragment, Fv, single chain Fv antibody ("scFv"), bis-scFv, (scFv)2, minibody, double antibody, triple antibody, quadruple antibody, disulfide bond stabilized Fv protein ("dsFv") and single domain antibody (sdAb, nanobody) or other antibody fragments thereof. In a preferred embodiment, the binding domain is scFv.

In one embodiment, the CAR includes an extracellular domain that binds to any one or any more of antigens selected from the following antigens: folate receptor α, 5T4, αvβ6 integrin, BCMA, B7-H3, B7-H6, CAIX, CD16, CD19, CD20, CD22, CD30, CD33, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, FRα, GD2, GD3, glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, IL-11Rα, IL-13Rα2, Lambda, Lewis-Y, Kappa, mesothelin, Muc1, Muc16, NCAM, NKG2D ligand, NY-ESO-1, PRAMS, PSCA, PSMA, ROR1, SSX, survivin, TAG72, TEM, VEGFR2 and WT-1.

In some embodiments, the CAR includes a linker residue between various domains. The "variable region linker sequence" is an amino acid sequence which links the heavy chain variable region to the light chain variable region and provides a spacer function which is compatible with the interaction of the two sub-binding domains, such that the obtained polypeptide reserves the same specific binding affinity of the target molecule as the antibody including the same light chain variable region and heavy chain variable region. In a specific embodiment, the linker separates one or more heavy chain variable domains or light chain variable domains, hinge domains, transmembrane domains, costimulatory domains and/or primary signaling domains. In a specific embodiment, the CAR includes one, two, three, four or five or more linkers. In a specific embodiment, the length of the linker is from about one amino acid to about 25 amino acids, from about 5 amino acids to about 20 amino acids, or from about 10 amino acids to about 20 amino acids or any amino acids having an intermediate length. In some embodiments, the length of the linker is 1, 2, 3, 4, 5, 6, 7, 8, 9, 10, 11, 12, 13, 14, 15, 16, 17, 18, 19, 20, 21, 22, 23, 24, 25 or more amino acids.

In one embodiment, behind the binding domain of the CAR are one or more "spacer domains", and the spacer domain refers to a region moving the antigen binding domain away from the surface of the effector cell to realize proper cell/cell contact, antigen binding and activation. The spacer domain can come from a natural, synthetic, semi-synthetic or recombination origin. In certain embodiments, the spacer domain is part of an immunoglobulin, including but not limited to one or more heavy chain constant regions, e.g., CH2 and CH3. The spacer domain may include an amino acid sequence of naturally occurring immunoglobulin hinge region or altered immunoglobulin hinge region. In one embodiment, the spacer domain includes CH2 and CH3 of IgG1, IgG4 or IgD.

The CAR also includes a transmembrane domain, and the transmembrane domain can come from a domain of natural, synthetic, semi-synthetic or recombination origin. In one embodiment, the transmembrane domain may include or be derived from one or more transmembrane regions in the following group: α or β chain of T cell receptor, CD3δ, CD3ε, CD3γ, CD3ζ, CD4, CD5, CD8α, CD9, CD16, CD22, CD27, CD28, CD33, CD37, CD45, CD64, CD80, CD86, CD134, CD137, CD152, CD154 and PD-1.

The CAR also includes an intracellular signaling domain, and the intracellular signaling domain transduces information of effective CAR binding to target antigens into the immune effector cells to trigger the effector cell function, for example, activation, cytokine production, proliferation, and cytotoxic activity, including releasing cytotoxicity factor to the target cells to which the CAR binds or other cell responses triggered by antigen binding to the extracellular CAR domain.

The intracellular signaling domain includes one or more "costimulatory signaling domains" and one "primary signaling domain"; a suitable primary signaling domain includes FcRγ, FcRβ, CD3γ, CD3δ, CD3ε, CD3ζ, CD22, CD79a, CD79b and CD66d.

"Costimulatory signaling domain" or "costimulatory domain" refers to intracellular signaling domain of a costimulatory molecule. A suitable costimulatory molecule includes TLR1, TLR2, TLR3, TLR4, TLR5, TLR6, TLR7, TLR8, TLR9, TLR10, CARD11, CD2, CD7, CD27, CD28, CD30, CD40, CD54(ICAM), CD83, CD134(OX40), CD137 (4-1BB), CD278(ICOS), DAP10, LAT, NKD2C, SLP76, TRIM and ZAP70.

DETAILED DESCRIPTION OF THE DISCLOSURE

In one aspect, the present disclosure provides a method for gene editing a PD1 gene in cells, the method includes the steps of gene editing the PD1 gene by using a nuclease and an sgRNA, and the sgRNA guides the nuclease to cleave the PD1 gene and forms a broken site.

Further, the targeting sequence of the sgRNA targeting PD1 contains the sequence shown in one or any more of SEQ ID NO: 1-6.

Further, the nuclease is selected from one or any more of Cas9, Cas3, Cas8a, Cas8b, Cas10d, Cse1, Csy1, Csn2, Cas4, Cas10, Csm2, Cmr5, Fok1 and Cpf1.

In a preferred embodiment, the nuclease is Cas 9; preferably, the Cas9 is selected from a Cas9 which is originated from *Streptococcus pneumoniae, Streptococcus pyogenes* or *Streptococcus thermophilus*.

In one embodiment, the sgRNA also includes chemical modification of bases. In a preferred embodiment, the sgRNA includes chemical modification of any one, any more or any more continuous bases at positions 1-n at 5' end, and/or chemical modification of any one, any more or any more continuous bases at positions 1-n at 3'end; the n is selected from 2, 3, 4, 5, 6, 7, 8, 9 or 10. Preferably, the sgRNA includes chemical modification of one, two, three, four or five bases at 5' end, and/or chemical modification of one, two, three, four or five bases at 3' end. For example, chemical modification is carried out on a base at position 1, a base at position 2, a base at position 3, a base at position 4, bases at position 5 or bases at positions 1-2, bases at positions 1-3, bases at positions 1-4, bases at positions 1-5 at 5' end of the sgRNA; and/or, chemical modification is carried out on a base at position 1, a base at position 2, a base at position 3, a base at position 4, a base at position 5 or bases at positions 1-2, bases at positions 1-3, bases at positions 1-4, bases at positions 1-5 at 3' end of the sgRNA. In a preferred embodiment, the chemical modification is one or any more of methylation modification, methoxy modification, fluorination modification or thiolizing modification.

The targeting sequence of the sgRNA includes one or any more of SEQ ID NO: 4-5.

More preferably, 2-methoxy modification and/or thiolizing modification are/is carried out on the first three bases at 5' end of the targeting sequence; more preferably, 2-methoxy modification and thiolizing modification are carried out on the first three bases at 5' end of the targeting sequence.

Further, the method further includes a step of providing a donor repair template.

Further, the donor repair template includes a homologous arm, the homologous arm includes a 5' homologous arm and/or a 3' homologous arm; preferably, the length of the 5' homologous arm is from 100 bp to 3000 bp, and the length of the 3' homologous arm is from 100 bp to 3000 bp.

Further, the donor repair template also includes an exogenous sequence.

Further, the donor repair template also includes a chimeric antigen receptor (CAR).

Further, the CAR includes an extracellular domain that binds to a specific target antigen, a transmembrane domain and an intracellular signaling domain.

Further, the antigen targeted by the extracellular domain is selected from one or any more of the following: folate receptor α, 5T4, αvβ6 integrin, BCMA, B7-H3, B7-H6, CAIX, CD16, CD19, CD20, CD22, CD30, CD33, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, FRα, GD2, GD3, glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, IL-11Rα, IL-13Rα2, Lambda, Lewis-Y, Kappa, mesothelin, Muc1, Muc16, NCAM, NKG2D ligand, NY-ESO-1, PRAME, PSCA, PSMA, ROR1, SSX, survivin, TAG72, TEM, VEGFR2 and WT-1.

Further, the transmembrane domain is selected from any one or any more transmembrane regions of the following: α or β chain of T cell receptor, CD3δ, CD3ε, CD3γ, CD3ζ, CD4, CD5, CD8a, CD9, CD16, CD22, CD27, CD28, CD33, CD37, CD45, CD64, CD80, CD86, CD134, CD137, CD152 and CD154.

Further, the intracellular signaling domain includes a costimulatory signaling domain and/or a primary signaling domain.

In a preferred embodiment, the cells are T cells.

Further, the method for introducing the nuclease, the sgRNA and the donor repair template into cells includes: vector transformation, microinjection, transfection, lipid transfection, heat shock, electroporation, transduction and gene gun; the vector transformation here should be understood as recombining the nuclease, the sgRNA or the donor repair template onto a vector, then transforming the vector into the cells; preferably, the electroporation method may be adopted. More preferably, the nuclease and the sgRNA form a complex, or the nuclease, the sgRNA and the donor repair template form a complex, and then the complex is introduced into the cells by the electroporation method.

In another aspect, the present disclosure also provides an sgRNA for gene editing a PD1 gene in cells.

In another aspect, the present disclosure also provides use of the above-described sgRNA in the gene editing of a PD1 gene in cells.

In another aspect, the present disclosure also provides gene-edited cells prepared by the above-described gene editing method.

In another aspect, the present disclosure also provides use of the gene-edited cells prepared by the above-described method in preparation of tumor immunotherapy or cancer immunotherapy products.

In one embodiment, when the gene-edited cells prepared by the above-described method are used in preparation of the tumor immunotherapy or cancer immunotherapy products, the cells are preferably T cells; in a preferred embodiment, the donor repair template for preparation of the above-described gene-edited T cells includes the chimeric antigen receptor (CAR).

Further, the tumor or cancer is selected from one or any more of the following: melanoma, Burkitt's lymphoma, leukemia, sarcoma, lymphoma, multiple myeloma, brain cancer, neuroblastoma, medulloblastoma, astrocytoma, glioblastoma, ovarian cancer, cervical cancer, uterine cancer, colorectal cancer, breast cancer, pancreatic cancer, lung cancer, gastric cancer, thyroid cancer, liver cancer, prostate cancer, esophagus cancer, kidney cancer, bladder cancer and gallbladder cancer.

The sgRNA provided by the present disclosure can achieve the efficient cleavage of the PD1 locus, achieve the efficient integration of exogenous sequences at a specific site of PD1, effectively improve the recombination efficiency of the exogenous sequences at the specific site of PD1, increase the stability of the sgRNA within the cells, reduce cell natural immune response caused by the sgRNA, and increase the cell viability.

Figures 2A, 2B:
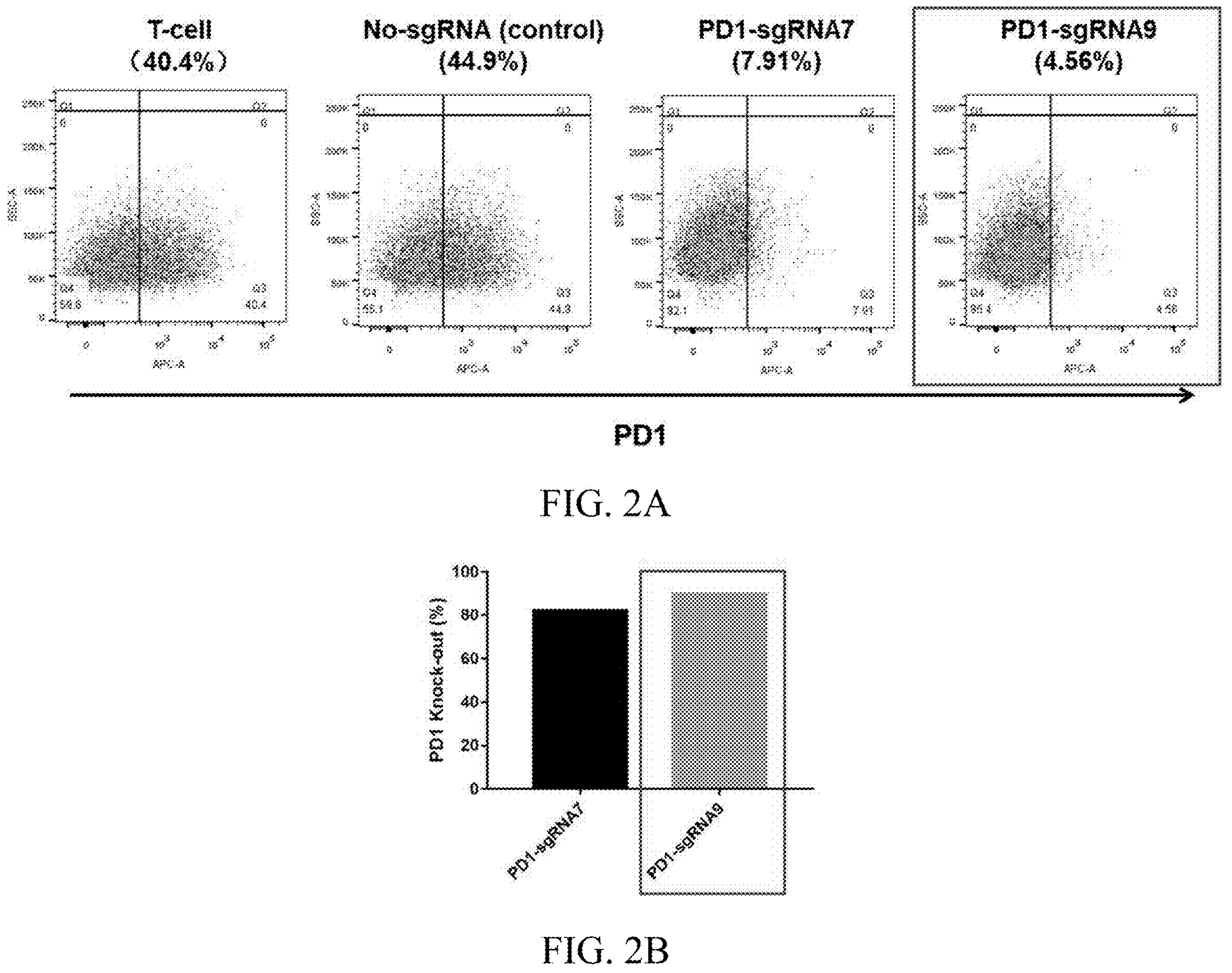

FIG. 2A shows screening of an sgRNA sequence for efficient cleavage of PD1 by a flow method; two sgRNAs (sgRNA7 and sgRNA9) targeting PD1 were respectively mixed with Cas9 protein, and then introduced into human T cells, and the cells were collected after 72 hours to detect the PD1 expression by the flow method and a knockout rate were calculated. FIG. 2B shows the knockout rate calculated.

Figure 3:
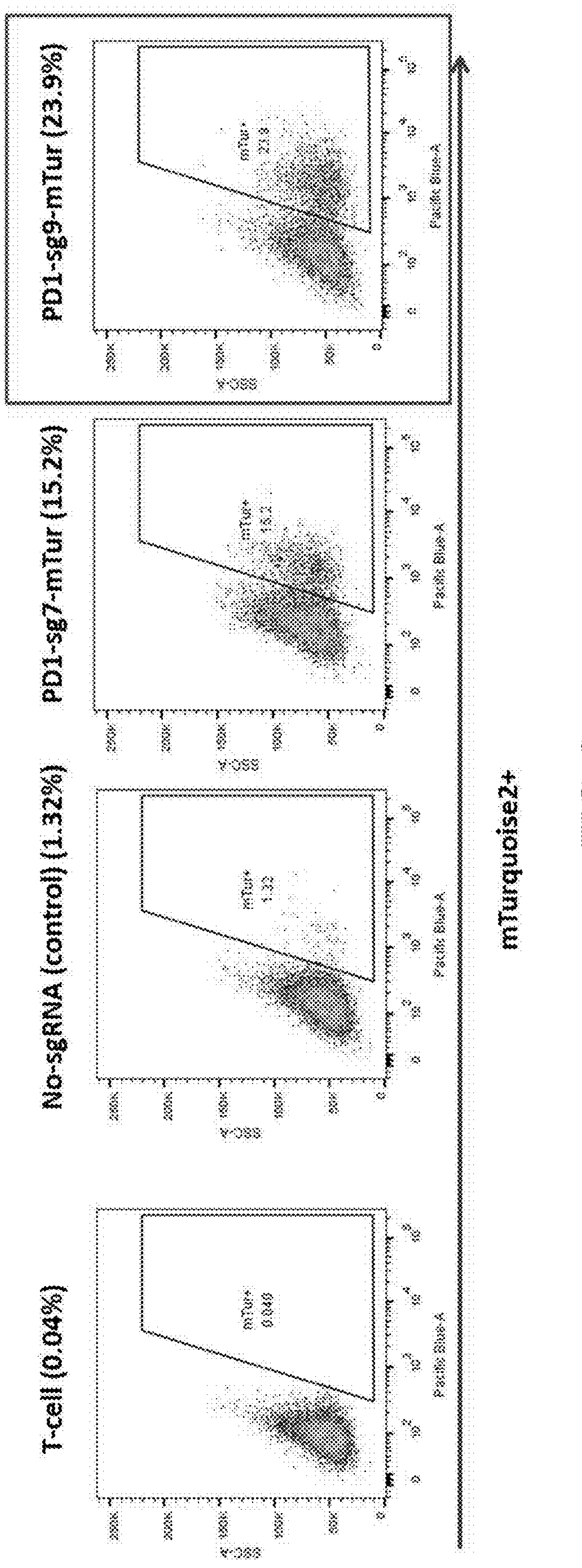

FIG. 3 shows detection of site-specific insertion efficiency by using a fluorescent protein reporter gene as an exogenous sequence; two gRNAs (sgRNA7 and sgRNA9) targeting PD1 were respectively mixed with Cas9 protein and an exogenous DNA sequence of the fluorescent protein reporter gene, and then introduced into human T cells, and the cells were collected after 7 days to detect the reporter gene integration rate by the flow method.

Figure 4:
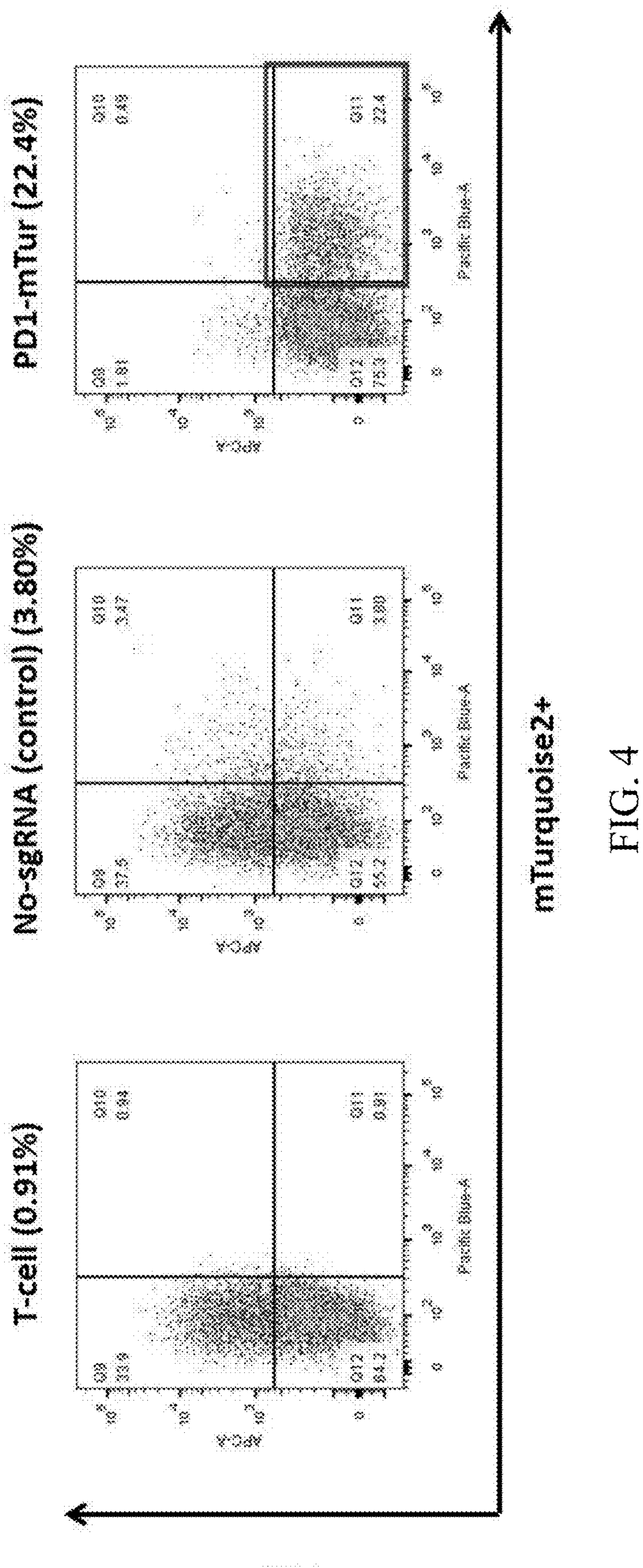

FIG. 4 shows that efficient knockout of the PD1 gene and efficient integration of the exogenous sequence can be simultaneously achieved at the PD1-sgRNA9 site; one efficient sgRNA (sgRNA9) targeting PD1 was mixed with Cas9 protein and an exogenous DNA sequence of the fluorescent protein reporter gene, and then introduced into human T cells, and the cells were collected after 3 days to detect the reporter gene integration rate and PD1 knockout rate by the flow method.

Figure 5:
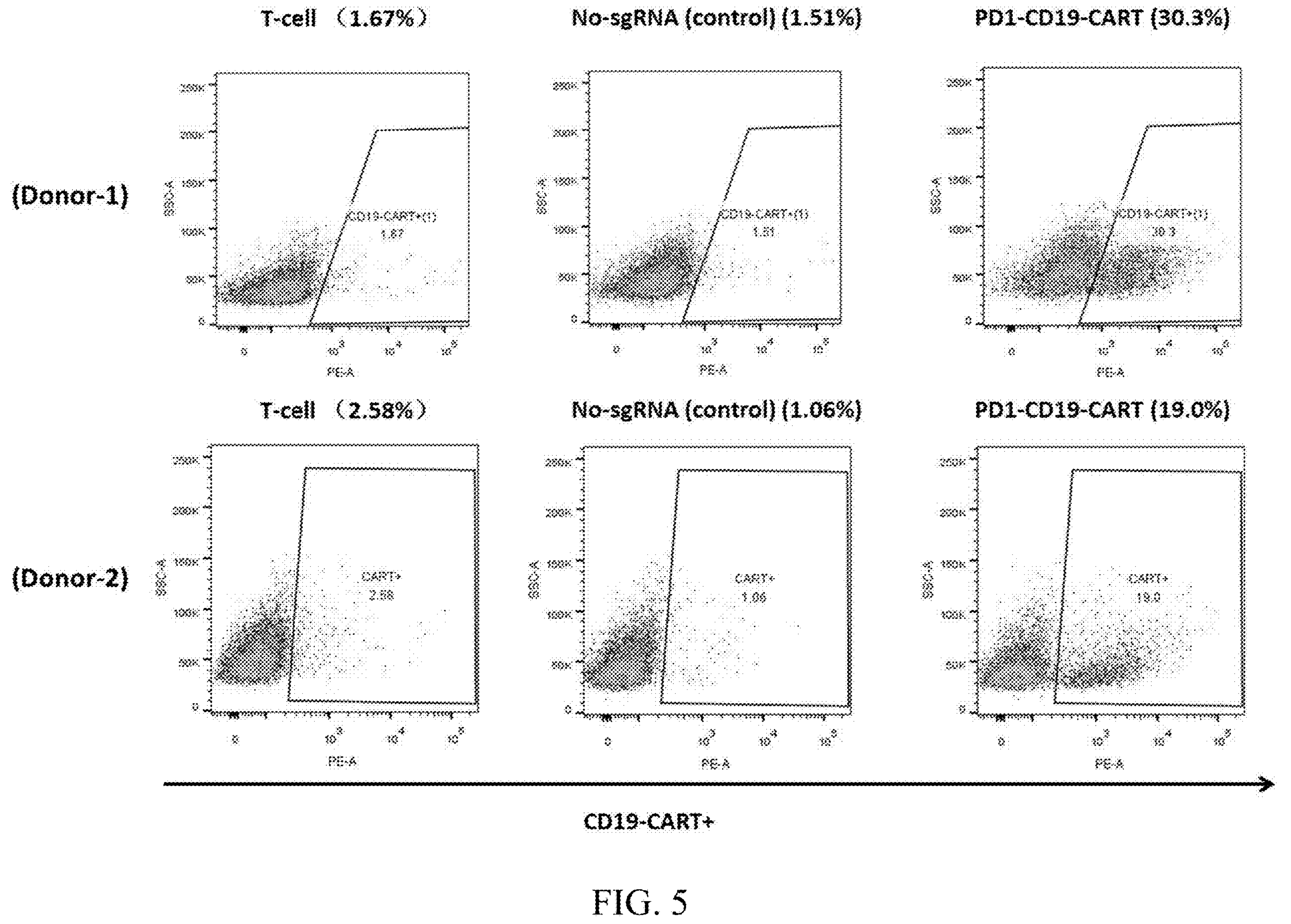

FIG. 5 shows detection of the positive rate of PD1 site-specific integrated CD19-CART by a flow method; one efficient sgRNA (sgRNA9) targeting PD1 was mixed with Cas9 protein and an exogenous DNA sequence of CD19-CART, and then introduced into human T cells of two different individual origins, and the cells were collected after 7 days to detect the integration rate of the CD19-CART by the flow method.

Figure 6A:
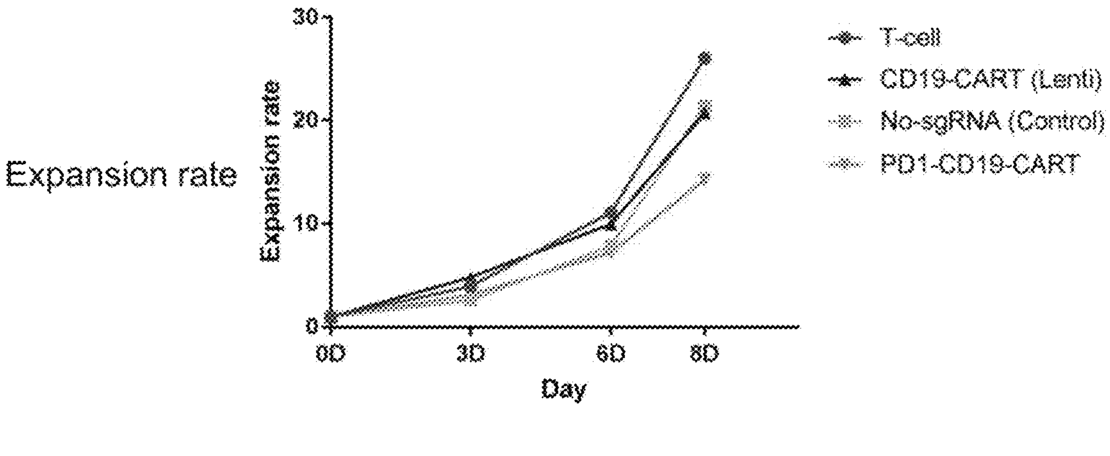
Figure 6B:
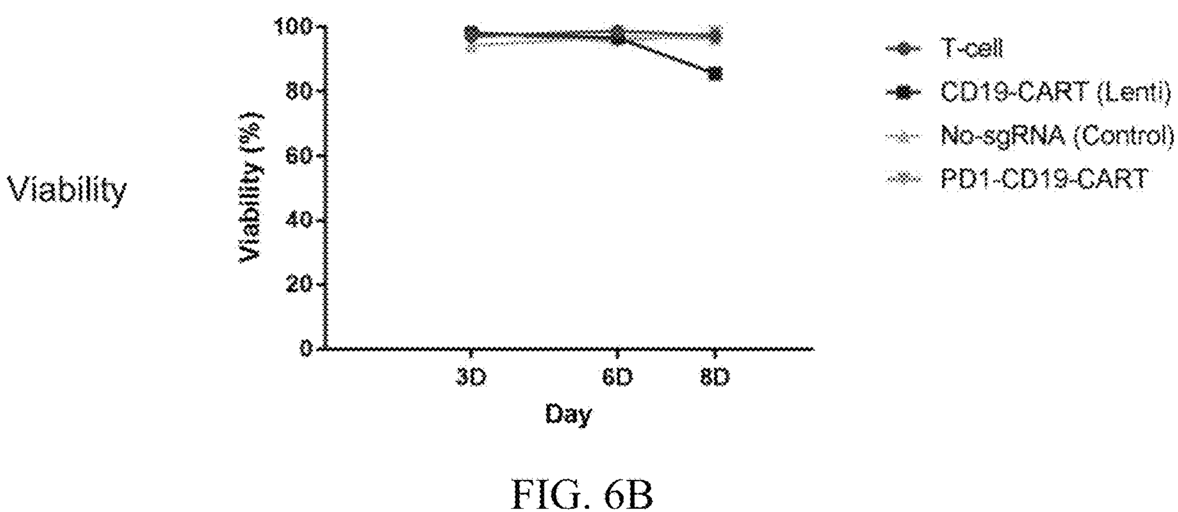

FIGS. 6A and 6B respectively show the expansion rate and viability of PD1 site-specific integrated CD19-CART; the in-vitro expansion rate and viability of PD1 site-specific integrated CD19-CART cells and CD19-CART cells prepared by a traditional lentivirus were compared.

Figure 7:
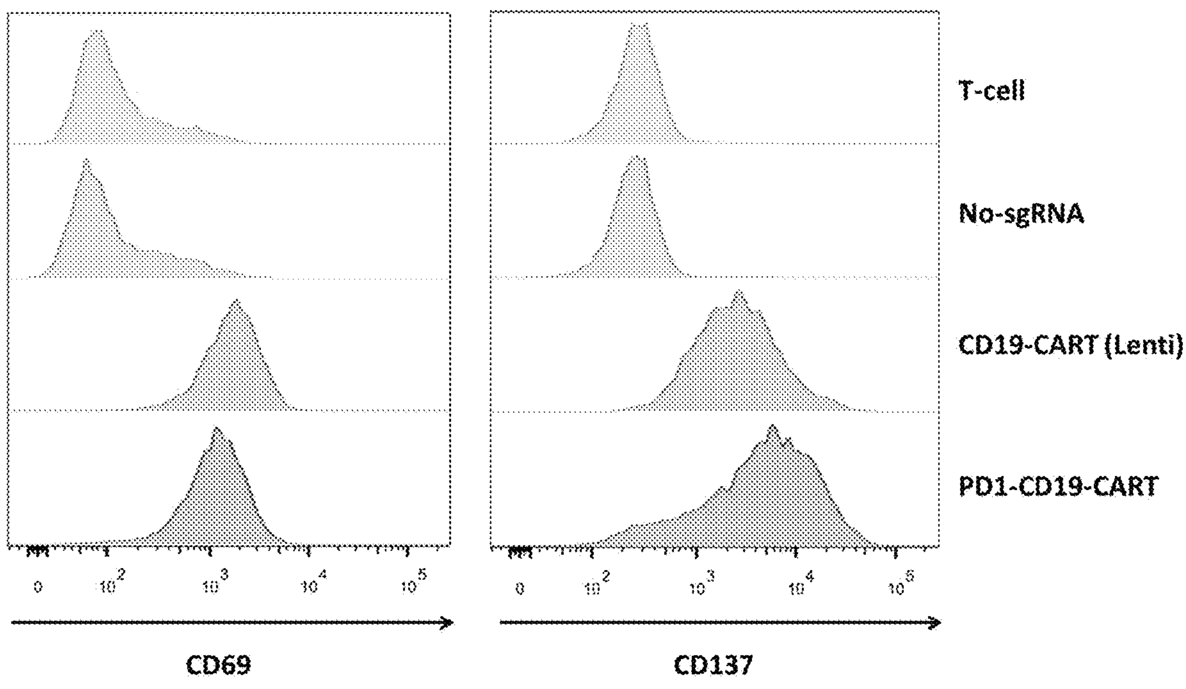

FIG. 7 shows T cell activation detection of PD1 site-specific integrated CD19-CART; PD1 site-specific integrated CD19-CART cells and CD19-CART cells prepared by lentivirus were respectively co-incubated with Raji tumor target cells over-expressing PDL1, and the cells were collected after 24 hours to detect the expression of T cell activation marker by the flow method; site-specific integrated CD19-CART with PD1 knockout can be constructed by using the sgRNA of the present disclosure, and compared with CD19-CART prepared by a traditional lentivirus method, the CAR-T cell activation degree of the site-specific integrated CD19-CART was shown to be better.

Figure 8:
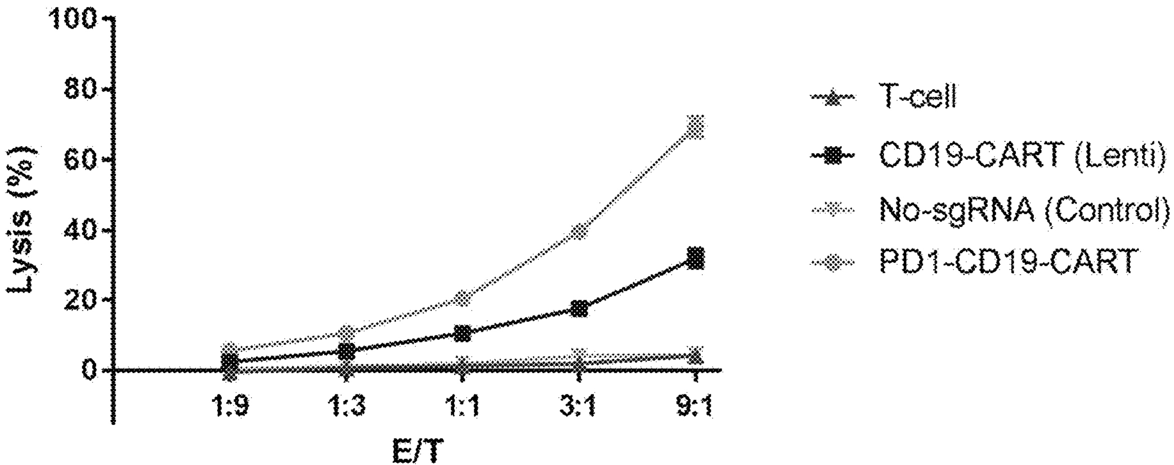

FIG. 8 shows in-vitro killing detection of PD1 site-specific integrated CD19-CART; PD1 site-specific integrated CD19-CART cells and CD19-CART cells prepared by the lentivirus were respectively co-incubated with Raji tumor target cells over-expressing PDL1, and in-vitro killing was detected by an LDH method; site-specific integrated CD19-CART with PD1 knockout can be constructed by using the sgRNA of the present disclosure, and compared with the CD19-CART prepared by a traditional lentivirus method, the CAR-T cells were shown to have a better in-vitro anti-tumor ability.

DETAILED DESCRIPTION OF THE EMBODIMENTS

The present disclosure will be further described in detail in conjunction with the following specific embodiments and drawings, and the protection content of the present disclosure is not limited to the following embodiments. Without departing from the spirit and scope of the inventive concept, changes and advantages occurring to those skilled in the art are all included in the present disclosure, and the appended claims are regarded as the protection scope. Processes, conditions, reagents, experimental methods, and the like for implementing the present disclosure, except for the contents specifically mentioned below, are all common knowledge and general knowledge in the art, and the present disclosure has no special restricted content, such as according to those recorded in Molecular cloning: A Laboratory Manual by Sambrook et al. (New York: Cold Spring Harbor Laboratory Press, 1989), or according to manufacturer's recommended conditions.

1. Design of sgRNAs:

(1) a human PD1 genomic sequence was queried via NCBI, exon 1, exon 2 or key protein coding region was selected for sgRNA design, and the targeting sequences of the designed sgRNAs are as follows:

```
sgRNA1:
                              (SEQ ID NO: 1)
tgtagcaccgcccagacgac

sgRNA3:
                              (SEQ ID NO: 2)
gtctgggcggtgctacaact

sgRNA4:
                              (SEQ ID NO: 3)
aggcgccctggccagtcgtc

sgRNA7:
                              (SEQ ID NO: 4)
gggcggtgctacaactgggc

sgRNA9:
                              (SEQ ID NO: 5)
cgactggccagggcgcctgt

sgRNA10:
                              (SEQ ID NO: 6)
ctacaactgggctggcggcc
```

(2) oligo of each sgRNA was synthesized, annealed, and linked to a PX458 vector.

2. Screening of Targets:

2-1. T7E1 Digestion:

(1) the Cas9 and the sgRNAs were transduced into the cells, and genome DNA was extracted;

(2) PCR primers were designed for the locations of the sgRNA targets, and a DNA fragment including the targets was obtained by PCR and purified by using a DNA gel extraction kit;

(3) T7E1 digestion analysis: the purified PCR product was annealed, and the annealing process are as follows:

| Temperature | Time |
|---|---|
| 95° C. | 5 minutes |
| 95° C.-85° C. | 2° C. reduced per second |
| 85° C.-25° C. | 0.1° C. reduced per second |

the annealed product was treated with T7E1 enzyme, and incubated for 30 minutes at 37° C., and a DNA Loading buffer was added to terminate the reaction;

(4) Polyacrylamide gel electrophoresis: a sample was added into a polyacrylamide gel, and a 1×TBE solution was added into an electrophoresis tank for electrophoresis under a constant voltage of 100V, until bromophenol blue run to the bottom of the polyacrylamide gel. The gel was taken out, placed in a TBE solution containing EB to soak for 10 minutes, and then the polyacrylamide gel was taken out for imaging under ultraviolet light;

(5) cleavage rates were analyzed according to grayscales, and efficient targets were selected.

2-2. Flow Detection of Knockout Rate:

(1) the Cas9 and the sgRNAs were transduced into cells, and the cells were collected after 2-3 days;

(2) after the cells were washed once with flow buffer, the cells were incubated with PD1 antibodies for staining, and incubated on ice for 30 minutes;

(3) the cells were washed twice with the flow buffer;

(4) the cells were re-suspended in the flow buffer with a suitable volume for flow computer analysis;

(5) change in PD1 expression quantity was detected, knockout rates were calculated, and efficient targets were selected.

2-3. Detection of Exogenous Sequence Recombination Rate:

(1) Cas9, sgRNAs and exogenous DNA were transduced into the cells, and the cells were collected after 7 days;

(2) after the cells were washed once with the flow buffer, the cells were incubated with antibodies capable of detecting the expression of exogenous proteins, etc. for staining, and incubated on ice for 30 minutes;

(3) the cells were washed twice with the flow buffer;

(4) the cells were re-suspended in the flow buffer with a suitable volume for flow computer analysis;

(5) proportion of the cells expressing the exogenous protein was detected, and targets with high recombination rates was selected.

Figure 1:
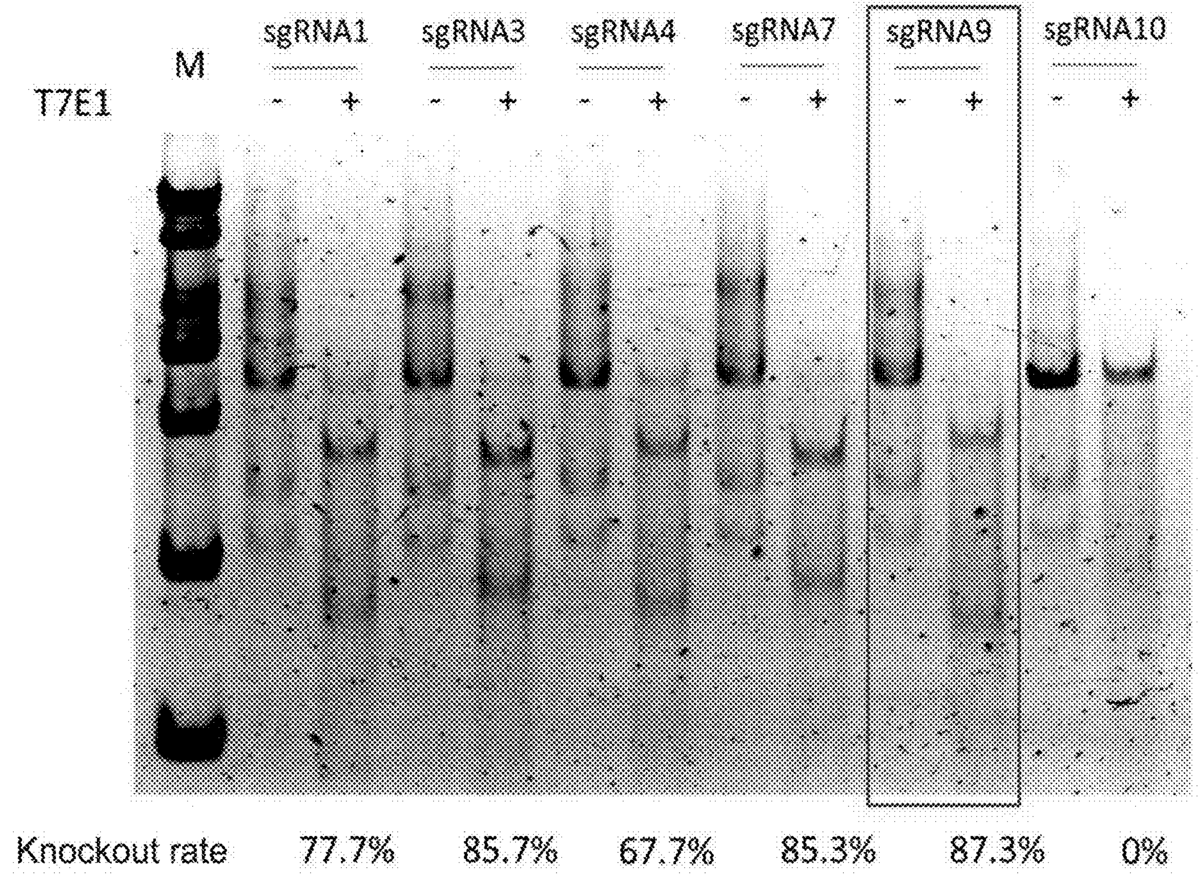
FIG. 1 shows screening of an sgRNA sequence for efficient cleavage of PD1 by a T7E1 method; 6 different sgRNAs (sgRNA1, sgRNA3, sgRNA4, sgRNA7, sgRNA9 and sgRNA10) targeting the PD1 were respectively mixed with the Cas9 protein, and then introduced into human T cells, and the cells were collected after 72 hours for T7E1 detection.

6 sgRNAs, i.e., sgRNA1, sgRNA3, sgRNA4, sgRNA7, sgRNA9 and sgRNA10 for the PD1 gene were used for verifying the knockout efficiency, as shown in FIG. 1, a T7E1 method was used to detect a knockout rate, and sgRNA3, sgRNA7 and sgRNA9 have a higher knockout rate (FIG. 1).

The flow method was continued to be used for verifying the knockout rate of sgRNA7 and sgRNA9. The result shows that both sgRNA7 and sgRNA9 have a higher knockout rate, and the result is consistent with that obtained through T7E1, as shown in FIGS. 2A-2B.

After that, an mTurquoise 2 fluorescent protein reporter gene was used as an exogenous donor sequence for detecting the efficiency of site-specific insertion of sgRNA7 and sgRNA9 at sites. The result shows that, sgRNA7 and sgRNA9 both can have higher site-specific integration efficiency, wherein the site-specific insertion efficiency of sgRNA7 reaches 15.2%, and the site-specific insertion efficiency of sgRNA9 reaches 23.9%, as shown in FIG. 3.

The flow cytometry was continued to be used for detecting the site-specific insertion of the sgRNA9, the result shows that, the fluorescent protein-positive cells for site-specific integration of the sgRNA9 are all PD1-negative cells (as shown in FIG. 4), which further confirms that this method can achieve the site-specific integration of an exogenous sequence.

3. Construction of Enhanced CD19-CART Cells with PD1 Knockout:

By using the sgRNA9 as an example below in combination with a CRISPR/Cas9 technology, the enhanced CD19-CART cells with PD1 knockout were constructed in one step.

3-1. SgRNA9 Preparation:

The sgRNA9 was synthesized, dissolved in a TE buffer, and diluted into a final concentration of 10 μg/μl;

3-2. Preparation of CD19-CART Site-Specific Integrated at PD1 by Using an Electrotransfection Method Instruments and Materials:

① Lonza 4D-Nucleofector™ System nucleofector

② the kit being P3 Primary Cell 4D-Nucleofector™ X Kit, Lonza, V4XP-3024

③ T cells 2-3 days after CD3/CD28 magnetic bead stimulation

④ commercial spCas9 protein (10 μg/μl) (Alt-R® S.p. Cas9 Nuclease 3NLS, IDT)

⑤ synthesized sgRNA9

Specific Operation Steps:

an electrotransfection cuvette suitable for a 100 μl size:

(1) According to 82 μl solution+18 μl supplement per electrotransfection cuvette, based on the total number of electrotransfection, one electrotransfection solution mix was prepared, mixed well, and placed at room temperature.

(2) Cas9 protein and sgRNA9 were co-incubated, and placed at room temperature for 10 minutes, to form an RNP.

(3) A "donor" exogenous donor DNA was added (including exogenous CD19-CART DNA of homologous arms) to the RNP, and incubated at room temperature for 2 minutes.

The CD19-CART includes an extracellular domain targeting CD19, a transmembrane region selected from CD8a and an intracellular signaling domain selected from CD3ζ and CD137; in addition, homologous arms were arranged at 5' and 3' ends of CD19-CART, and the upstream and downstream homologous arm sequences are respectively shown in SEQ ID NO: 7 and SEQ ID NO: 8.

(4) T cells in activated state were collected, and were subjected to an electrotransfection reaction at intervals of a count of 5×106.

(5) The cells and the "RNP+donor" were mixed well and re-suspended, and then added into the electrotransfection cuvette.

(6) An electrotransfection instrument was turned on, the electrotransfection cuvette was put into a slot, and a corresponding procedure (Stimulated human T cell) was chosen for the electrotransfection.

(7) The cells were added into a preheated cell culture medium, and incubated in a cell incubator.

3-3. Evaluation of PD1 Site-Specific Integrated CD19-CART Cells

Using the above-described "donor" exogenous donor DNA as an exogenous DNA sequence, it is confirmed in T cells of two different donors (Donor-1 and Donor-2) that T cells all have high site-specific integration rates at the PD1-sgRNA9 site, as shown in FIG. 5, and the site-specific integration efficiency reaches 20%-30%.

In addition, compared with the CD19-CART cells (CD19-CART (Lenti)) prepared by the traditional lentivirus, the PD1 site-specific integrated CD19-CART cells (PD1-CD19-CART) are equivalent in cell expansion rate, as shown in FIG. 6A; however, compared with the CD19-CART cells prepared by the traditional lentivirus, the PD1 site-specific integrated CD19-CART cells exhibit a higher cell viability, as shown in FIG. 6B.

By Co-incubating the PD1 site-specific integrated CD19-CART cells and the CD19-CART cells prepared by the lentivirus with Raji tumor cells (Burkitt's Lymphoma cell) over-expressing PDL1, expression of T cell activated markers CD69 and CD137 were detected by the flow method, the result shows that compared with CD19-CART cells (CD19-CART(Lenti)) prepared by the traditional lentivirus, the PD1 site-specific integrated CD19-CART cells (PD1-CD19-CART) have a similar CD69 expression and higher CD137 expression, as shown in FIG. 7.

In-vitro killing was detected by using an LDH method, it is observed that compared with CD19-CART cells (CD19-CART (Lenti)) prepared by the traditional lentivirus, the PD1 site-specific integrated CD19-CART cells (PD1-CD19-CART) have a stronger ability of killing Raji tumor cells over-expressing PDL1, as shown in FIG. 8.

In conclusion, by using the sgRNA of the present disclosure, in conjunction with the CRISPR/Cas9 technology, the site-specific integrated CD19-CART cell with PD1 knockout can be constructed in one step. Compared with the traditional lentivirus method, this method can reduce the high cost resulting from use of viruses in the CAR-T preparation process, greatly reducing the treatment expense of the CAR-T therapy. In another aspect, this method enables CAR-T elements to be directionally inserted into a specific site of the PD1 locus, so that the potential safety hazard resulting from random virus insertion. Furthermore, this method can construct the enhanced CD19-CART cells with PD1 knockout in one step, so that the anti-tumor ability of the CAR-T cells can be improved. This embodiment proves the importance and value of the sgRNA protected by the present disclosure, but it is not limited to directional insertion of CD19-CART exogenous sequences at the specific site of PD1, and can be extended to other CART sequences and used in development of other therapies of immunotherapy.

What is claimed is:

1. A method for gene editing a PD1 gene in cells, comprising the steps of introducing a nuclease and an sgRNA into the cells, and gene-editing the PD1 gene, wherein the sgRNA guides the nuclease to cleave the PD1 gene and forms a broken site, wherein the method comprises the steps of providing and introducing a donor repair template into the broken site of the cells in a non-viral manner;

wherein a targeting sequence of the sgRNA comprises at least one sequence selected from the group consisting of SEQ ID NOs: 1-5.

2. The method according to claim 1, wherein the nuclease is at least one selected from the group consisting of Cas9, Cas3, Cas8a, Cas8b, Cas10d, Cse1, Csy1, Csn2, Cas4, Cas10, Csm2, Cmr5, Fok1, and Cpf1, wherein when the nuclease is Cas9, the Cas9 is selected from Cas9 originated from *Streptococcus pneumoniae, Streptococcus pyogenes*, or *Streptococcus thermophilus*.

3. The method according to claim 1, wherein the sgRNA comprises at least one chemical modification of bases selected from the group consisting of methylation modification, methoxy modification, fluorination modification, and thiolizing modification.

4. The method according to claim 1 further comprising the steps of providing a donor repair template and introducing the donor repair template into the cells, wherein the donor repair template comprises a chimeric antigen receptor (CAR).

5. The method according to claim 4, wherein the CAR comprises a transmembrane domain, an intracellular signaling domain, and an extracellular domain binding to a specific target antigen.

6. The method according to claim 5, wherein the specific target antigen targeted by the extracellular domain is at least one selected from the group consisting of the following: folate receptor $\alpha$, 5T4, $\alpha v\beta 6$ integrin, BCMA, B7-H3, B7-H6, CAIX, CD16, CD19, CD20, CD22, CD30, CD33, CD44, CD44v6, CD44v7/8, CD70, CD79a, CD79b, CD123, CD138, CD171, CEA, CSPG4, EGFR, EGFR family including ErbB2 (HER2), EGFRVIII, EGP2, EGP40, EPCAM, EphA2, EpCAM, FAP, fetal AchR, FR$\alpha$, GD2, GD3, glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, IL-11Ra, IL-13R$\alpha$2, Lambda, Lewis-Y, Kappa, mesothelin, Muc1, Muc16, NCAM, NKG2D ligand, NY-ESO-1, PRAME, PSCA, PSMA, ROR1, SSX, survivin, TAG72, TEM, VEGFR2, and WT-1;

the transmembrane domain is at least one selected from the group consisting of the following transmembrane regions: $\alpha$ chain of T cell receptor, $\beta$ chain of the T cell receptor, CD38, CD3$\varepsilon$, CD3$\gamma$, CD3$\zeta$, CD4, CD5, CD8$\alpha$, CD9, CD16, CD22, CD27, CD28, CD33, CD37, CD45, CD64, CD80, CD86, CD134, CD137, CD152, and CD154; and the intracellular signaling domain comprises a costimulatory signaling domain and/or a primary signaling domain, wherein the primary signaling domain comprises at least one selected from the group consisting of FcR$\gamma$, FcR$\beta$, CD3$\gamma$, CD3$\delta$, CD3$\varepsilon$, CD3$\zeta$, CD22, CD79a, CD79b, and CD66d, and the costimulatory signaling domain is at least one selected from the group consisting of TLR1, TLR2, TLR3, TLR4, TLR5, TLR6, TLR7, TLR8, TLR9, TLR10, CARD11, CD2, CD7, CD27, CD28, CD30, CD40, CD54 (ICAM), CD83, CD134 (OX40), CD137 (4-1BB), CD278 (ICOS), DAP10, LAT, NKD2C, SLP76, TRIM, and ZAP70.

7. The method according to claim 4, wherein the method for introducing the nuclease, the sgRNA, and the donor repair template into the cells comprises: vector transformation, transfection, heat shock, electroporation, transduction, gene gun, and microinjection;

wherein when a complex is formed from the nuclease and the sgRNA, or from the nuclease, the sgRNA, and the donor repair template, and the complex is introduced into the cells by electroporation.

8. The method according to claim 1, wherein the cells are T cells.

9. A method for gene editing a PD1 gene in cells, comprising the steps of introducing a nuclease and an sgRNA into the cells, and gene-editing the PD1 gene, wherein the sgRNA guides the nuclease to cleave the PD1 gene and forms a broken site, wherein the method comprises the steps of providing and introducing a donor repair template into the broken site of the cells in a non-viral manner; wherein the targeting sequence of the sgRNA comprises SEQ ID NO: 5.

* * * * *

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial sequence
<220> FEATURE:
<223> OTHER INFORMATION: targeting sequence of sgRNA1

<400> SEQUENCE: 1

tgtagcaccg cccagacgac                                                    20


<210> SEQ ID NO 2
<211> LENGTH: 20
<212> TYPE: DNA
<213> ORGANISM: Artificial sequence
<220> FEATURE:
<223> OTHER INFORMATION: targeting sequence of sgRNA3

<400> SEQUENCE: 2

gtctgggcgg tgctacaact                                                    20


<210> SEQ ID NO 3
<211> LENGTH: 20
<212> TYPE: DNA
<213> ORGANISM: Artificial sequence
<220> FEATURE:
<223> OTHER INFORMATION: targeting sequence of sgRNA4

<400> SEQUENCE: 3

aggcgccctg gccagtcgtc                                                    20


<210> SEQ ID NO 4
<211> LENGTH: 20
<212> TYPE: DNA
<213> ORGANISM: Artificial sequence
<220> FEATURE:
<223> OTHER INFORMATION: targeting sequence of sgRNA7

<400> SEQUENCE: 4

gggcggtgct acaactgggc                                                    20


<210> SEQ ID NO 5
<211> LENGTH: 20
<212> TYPE: DNA
<213> ORGANISM: Artificial sequence
<220> FEATURE:
```

<223> OTHER INFORMATION: targeting sequence of sgRNA9

<400> SEQUENCE: 5
cgactggcca gggcgcctgt 20

<210> SEQ ID NO 6
<211> LENGTH: 20
<212> TYPE: DNA
<213> ORGANISM: Artificial sequence
<220> FEATURE:
<223> OTHER INFORMATION: targeting sequence of sgRNA10

<400> SEQUENCE: 6
ctacaactgg gctggcggcc 20

<210> SEQ ID NO 7
<211> LENGTH: 800
<212> TYPE: DNA
<213> ORGANISM: Artificial sequence
<220> FEATURE:
<223> OTHER INFORMATION: Upstream homologous arm of CD19-CART

<400> SEQUENCE: 7
ccaggaagag gctccctctc tcctcgatcc gggagagtga ggccaaggcc tcccccacgg 60
atggtctgaa cagggctcgg ggagagccct ggaatctggg cagagaccca ggcgggcaca 120
atccccaccc aggagggatc ctggagacag aagaactgtc ctcactcgaa caggtacact 180
ttggatataa tgagaaaaat atcaccagct catctaaact ttgacgtcgt aaagccaagg 240
ttagtcccac atggggctca tcccatcctt aggaaaactc gagtgaggac caaggatgcc 300
tgggcaaggc agagccgcca cgcagactcc ccacggccaa ggtttggggt tctggccagc 360
ctgacccgtc attctacaga aacacgcagc cccaaggacc ggctgagagg ggacagaggt 420
cctgcctgcc caggagcaaa gaggggactt gggccagggg aggagttggg gcccagagag 480
gaacccagga gttcgagctg cccaaagcca cacagctcag ggtaaggggc agagctgggg 540
gccaaggctg ggcctgccac agcacccccc gacctgccag ggactgagag tgaaaggtcc 600
ctccagaccc ctcgctccgg gacccctggg ctgccagggc caggcccgcc tcagcacccc 660
ccgacctgcc agggactgag ggtggaaggt ccctccagac ccctggctct gggacacctg 720
accgccgacc ccacctacct aagaaccatc ctggccgcca gcccagttgt agcaccgccc 780
agacgactgg ccagggcgcc 800

<210> SEQ ID NO 8
<211> LENGTH: 800
<212> TYPE: DNA
<213> ORGANISM: Artificial Sequence
<220> FEATURE:
<223> OTHER INFORMATION: Downstream homologous arm of CD19-CART

<400> SEQUENCE: 8
tgtgggatct gcatgcctgg agcagcccca ccagagtgcc gccttctcca ctgctcaggc 60
ggaggtgagc ggaagggaaa ctgtcccagg tcaggttgaa gggagggtgc ccgccccttg 120
ctcccgcccc ctcttcctcc acatccacgt gggcgagagt gacagaggca gtgctggggg 180
aggaggggtg aggagggggt aggactgggg agagggtggg ggagggagag agagacagag 240
acagggagac agaggagatg gggaggaggt gggcccgtgg cccccacgcc ctaccccgtg 300
ggggtctccc cagctcaggg ccccttcctc ctctgtgtct ctgctcactg ctgtggcctc 360
tttccatatc ccgcccgagc tgcccctcct gaggctgccg ggtgggggca ggcccttctc 420

-continued

```
ctcccccatc ccccccatct ccctgggggc cgggcctccc tgcctgggga aggtgggtgg    480

ccccctctgg gctcaggttc ctgggctgca gtgaggggtg ggctcaaccc cactcccatt    540

ctgtcggagc ctctgggagc ctcccggctg cccacagcct ctgcccctgc tgggggcagg    600

tgcctggcct ctgccttccc ggcccatccc ccttcgctgg ggcacaggtg accctactga    660

atgacaactg tccatggcta atcggctccc cctcaaagct tccaccttgt ggatggcctc    720

acaccatggc cacagttcca gatctttcca ccgtgtgatg cctgcaacag cctgacgggg    780

gggctggggc ggtggcaggg                                                800
```